United States Patent [19]

Schumacher et al.

[11] Patent Number: 5,312,743
[45] Date of Patent: May 17, 1994

[54] CHOLESTEROL ESTERASES WITH VARIABLE SUBSTRATE SPECIFICITY

[75] Inventors: Günther Schumacher, Bernried; Christian Hanke, Eberfing; Stephan Fischer, Polling, all of Fed. Rep. of Germany

[73] Assignee: Boehringer Mannheim GmbH, Mannheim-Waldhof, Fed. Rep. of Germany

[21] Appl. No.: 828,980
[22] PCT Filed: Jun. 6, 1991
[86] PCT No.: PCT/EP91/01089
 § 371 Date: Jan. 29, 1992
 § 102(e) Date: Jan. 29, 1992
[87] PCT Pub. No.: WO91/18997
 PCT Pub. Date: Dec. 12, 1991

[30] Foreign Application Priority Data

Jun. 6, 1990 [DE] Fed. Rep. of Germany ....... 4018152

[51] Int. Cl.$^5$ ................ C12N 15/00; C12N 15/55; C12N 9/18; C12Q 1/44; C12Q 1/60
[52] U.S. Cl. .................. 435/172.3; 435/11; 435/19; 435/69.1; 435/71.2; 435/172.1; 435/197; 935/10; 935/14; 935/29; 935/56; 935/72; 536/23.2
[58] Field of Search ............... 435/11, 19, 69.1, 71.2, 435/172.1, 172.3, 197; 935/10, 14, 29, 56, 72; 536/23.2

[56] References Cited

FOREIGN PATENT DOCUMENTS 0260105 3/1988 European Pat. Off. .

OTHER PUBLICATIONS

G. Gibney et al. "Mutagenesis of Essential Functional Residues in . . . " Proc. Natl. Acad. Sci. 87: 7546–7550 (Oct. 1990).

T. Uwajima et al. "Purification and Properties of Cholesterol Esterase . . . " Agric. Biol. Chem. 40(10) 1957–1964 (1976).

A. J. Poulose et al. "Alteration of Substrate Specificity of a Lipase . . . " Abstract Papers of the Chemical Congress, North America BTEC 47(1988).

W. H. Rastetter "Enzyme Engineering: Applications and Promise" Trends in Biotechnology 1(3) 80–84 (1983).

R. M. Tel et al. "Incomplete Hydrolysis of Cholestryl Estes . . . " J. Clinical Chem., and Clin. Biochem. 18(10) 595–601 (Oct. 1980) (See Medline Abstract).

W. Kugimiya et al. "Molecular Cloning and Nucleotide Sequence . . . " Biochem. Biophys. Res. Commun. 141(1) 185–190 (Nov. 1986).

Primary Examiner—Robert A. Wax
Assistant Examiner—Rebecca Prouty
Attorney, Agent, or Firm—Felfe & Lynch

[57] ABSTRACT

For the preparation of cholesterol esterases with variable substrate specificity by cloning of a cholesterol esterase gene, the active center of which has the sequence -Gly-His-Ser-X-Gly-, wherein X signifies an amino acid, into a vector, transformation of a microorganism with this vector and expression of the cholesterol esterase gene, one exchanges the amino acid X of the active center for another amino acid by mutagenesis.

13 Claims, No Drawings

CHOLESTEROL ESTERASES WITH VARIABLE SUBSTRATE SPECIFICITY

The invention concerns a process for the preparation of cholesterol esterases with changed substrate specificity, with cholesterol esterases obtained in this way, as well as with their use for the enzymatic determination of cholesterol.

The determination of cholesterol in serum is an important parameter in the diagnosis of arteriosclerosis. The cholesterol present in serum is present in very heterogeneous compounds, whereby about 70 to 80% of the cholesterol is esterified with fatty acids of varying length. Thus, the exact determination of the cholesterol level depends upon how completely the cholesterol esters present are cleaved to free cholesterol. In clinical and medical practice, the enzymatic cleavage of the cholesterol esters by means of cholesterol esterase has proven to be the simplest process. However, it is a disadvantage of this determination that different cholesterol esters are cleaved by particular cholesterol esterases with differing specificity. Therefore, it is an object of the invention to make available cholesterol esterases with changed substrate specificity and improved activity.

According to the invention, this task is solved by a process for the preparation of cholesterol esterases with changed substrate specificity by cloning of a cholesterol esterase gene, the active site of which has the sequence -Gly-His-Ser-X-Gly-, wherein X signifies an amino acid, into a vector, transformation of a micro-organism with this vector and expression of the cholesterol esterase gene, which is characterised in that one exchanges the amino acid X of the active site for another amino acid by mutagenesis.

The invention concerns cholesterol esterases which, as active site (i.e. as region responsible for the enzymatic activity) contains the amino acid sequence -Gly-His-Ser-X-Gly-, whereby X signifies any desired amino acid. Such cholesterol esterases with different amino acid residues X are known (see e.g. Table 1). However, these cholesterol esterases originate from different organisms and, consequently, also differ in the nucleotide sequence of the genes coding therefor. According to the present invention, a process is now made available for obtaining a batch of different cholesterol esterases from a single cholesterol esterase in a simple and rapid manner by mutagenesis of the amino acid X of the active site, which only differ in the amino acid X. However, by the change of the nucleotide sequences in the cholesterol esterase gene, at the same time an additional change of the peptide frame outside of the active site can also take place insofar as this is desired.

Surprisingly, it has been found that the substrate specificity of cholesterol esterases, the active site of which has the amino acid sequence -Gly-His-Ser-X-Gly-, can be changed in that one exchanges the amino acid X in the active site by another amino acid. This is expediently achieved by mutation of the codon which codes for the amino acid X in the active site. The mutagenesis is preferably carried out in an objective manner, namely, with the use of oligonucleotides. One cuts out from the cholesterol esterase gene an oligonucleotide which contains the coding region for the active site and, in place thereof, ligates a new oligonucleotide into the gene which, in the place of X, codes for another amino acid.

The new oligonucleotide is preferably synthesised by chemical means. The synthesis is expediently carried out on a solid phase. Such solid phase methods are described summarily in E.-L. Winnacker, Gene und Klone, VCH Verlagsgesellschaft Weinheim (1985), pages 44 et seq. The new oligonucleotide is expediently prepared according to the amidite process, especially the phosphoramidite process.

Alternatively to the chemical synthesis, it has also proved to be expedient to obtain the new oligonucleotide from genes or gene of building blocks of other lipase/cholesterol esterases. One usually proceeds in a manner such that one selects the gene from such a lipase/cholesterol esterase which already displays the substrate specificity for the desired ester bond. From such a gene the nucleotide sequence coding for the active centre is cut out and is introduced into the cholesterol esterase gene to be changed as new active centre.

In the process according to the invention, there is preferably used the cholesterol esterase gene which corresponds to the amino acid sequence according to SEQ ID NO:1.

In the process according to the invention, it has also proven to be expedient that, for the transformation and for the expression of the cholesterol esterase gene, a micro-organism is used which itself does not express an active cholesterol esterase. As such a micro-organism, there is particularly used a Pseudomonas or *E. coli* strain, especially preferably Pseudomonas spec. DSM 5902. Micro-organisms which do not express a cholesterol esterase can be produced by by mutagenizing a strain which produces cholesterol esterase so that it no longer expresses active cholesterol esterase. This strain is then transformed with a vector (e.g. a plasmid) which carries the gene for the cholesterol esterase with changed substrate specificity.

However, it is also possible to carry out the process according to the invention with a strain of a micro-organism which expresses cholesterol esterase. In comparison with the original strain, such a strain will then display increased expression. In the process according to the invention, for this purpose there are preferably used, as starting strains, *E. coli* or Pseudomonas strains.

According to the invention, as vectors for the cholesterol esterase gene, there are preferably used pBR322, pUC18 or pBT306.1 (EP-A-0 187 138).

In the process according to the invention, as codon for the variable amino acid X, there is preferably used, in each case, the codon which is also present in the corresponding micro-organism or vector. However, it has proved to be especially expedient to use as codon for X, for His CAT, for Met ATG, for Phe TTC, for Gln CAG, for Leu TTG, for Ile ATC, for Val GTC, for Ser TCT, for Pro CCC, for Thr ACT, for Ala GCT, for Tyr TAT, for His CAC, for Asn AAC, for Lys AAG, for Asp GAC, for Glu GAG, for Cys TGT, for Arg CGT and for Gly GGA.

The amino acid introduced by the mutation preferably is Leu, Gln, Met or His. The amino acid Gln is especially preferred.

The invention also concerns new, hitherto unknown cholesterol esterases which are obtainable via the process according to the invention. In particular, however, the invention concerns a mixture of those cholesterol esterases obtainable by the process according to the invention which cleave every cholesterol ester bond. According to the invention, this can be achieved in that one produces cholesterol esterases which contain in the active centre all 20 amino acids possible for X. With a mixture of such cholesterol esterases according to the invention, preferably a mixture of all 20 different cholesterol esterases, it is possible to completely cleave in a simple manner completely the various cholesterol esters occurring in the body.

Therefore, the invention also concerns the use of cholesterol esterases obtained in this way for the determination of cholesterol in body fluids, as well as a reagent which contains these or a mixture thereof.

The strain *Pseudomonas spec.* DSM 5902 and the plasmid pBTmglCE with the deposit number DSM 5903 were deposited on the 24th Apr., 1990, at the Deutsche Sammlung von Mikroorganismen (DSM) (German Collection of micro-organisms), Mascheroder Weg 1b, D-3300 Braunschweig. The *Escherichia coli* strain HB 1254 with the deposit number DSM 6541, has been deposited on the 29.05.1991 at the Deutsche Sammlung von Mikroorganismen.

The invention is explained in more detail by the following Examples, in conjunction with the sequence protocols.

SEQ ID NO:1 shows the amino acid sequence of the cholesterol esterase of *Pseudomonas spec.*

SEQ ID NO:2 and 3 show 2 complementary oligonucleotides which together give an EcoRI/SalI fragment which codes for amino acids 1 to 30 of the mature cholesterol esterase.

SEQ ID NO:4 and 5 show the oligonucleotides used for the fusion of the cloned cholesterol esterase to the GBP signal peptide via a deletion mutagenesis.

EXAMPLE 1

Cloning of the *Pseudomonas spec.* gene which codes for cholesterol esterase (CE)

DNA was isolated from a micro-organism of the genus Pseudomonas, digested with suitable restriction enzymes and cloned into a vector compatible for *E. coli*, such as pBR 322. The identification of CE-containing plasmids took place via oligonucleotides which were derived from the peptide sequence of the *Pseudomonas spec.* cholesterol esterase. With the use of oligonucleotide samples which were derived from the amino terminus of the CE protein, there was isolated a 2.1 kb-sized PstI fragment of the *Pseudomonas spec.* DNA which was then subcloned into pBR322. DNA sequencing showed that this fragment only coded the N-terminal part of the cholesterol esterase. With the help of the PstI fragment as sample, the C-terminal part of the CE-coding DNA was identified on an approximately 1.1 kb-sized SalI fragment and also subcloned into pBR322.

The amino acid sequence of the overlapping PstI and SalI fragments derived from the DNA gave an open reading frame of 316 amino acids. The molecular weight of the mature protein is 30770 D.

Cholesterol esterase is an enzyme localised in the periplasma or the outer membrane. A signal peptide of 24 amino acids is responsible for its secretion. The protein sequences, which were found by sequencing various preparations of the enzyme isolated from *Pseudomonas spec.* and purified, are themselves not homogeneous. At the +1 position of the mature cholesterol esterase either the amino acid Phe or Trp (see SEQ.ID.NO:1) can be positioned, whereby there is given a signal peptide cleavage position is located between amino acid 24 and 25 or between amino acid 25 and 26. Therefore, in the case of expression in *E. coli*, account is to be taken of the fact that the N-terminus can be variable.

Signal peptide cleavage positions should be used which are recognized in *E. coli* (Van Heijne, Eur. J. Biochem., 133 (1983), 17–21; Van Heijne, J. Mol. Biol., 184 (1985), 99–105). The vector M13mglEcoK (cf. WO 88/09373) contains such a signal peptide cleavage position. This vector contains an about 700 bp-sized EcoRI/BamHI DNA fragment from the mgl operon from S. typhimurium (Benner-Luger and Boos, Mol. Gen. Genet., 214 (1988), 579–587) which contains not only the promoter but also the translation initiation region and the signal peptide of the galactose binding protein (GBP). The cleavage position of this signal peptide is frequently used in *E. coli* (Van Heijne, Eur. J. Biochem., 133 (1983), 17–21).

For the completion of the C-terminal 1.1 kb-sized SalI fragment of the cholesterol esterase, two complementary oligonucleotides (see SEQ.ID.NO.:2 and 3, corresponding to the amino acid Phe on position +1 up to the amino acid Val in position +30) were inserted into the vactor pUC18, whereby pUC18* resulted. The 1.1 kb-sized SalI fragment of the cholesterol esterase sub-cloned into pBR322 was cloned into pUC18* which had been linearized with SalI. The plasmid pCHE1 thereby results.

For the fusion to the GBP signal peptide, the cholesterol esterase gene cloned into pCHE1 was subcloned into the vector M13mglEcoK. For this purpose, the vector M13mglEcoK was cleaved with KpnI, the overlapping 3'-end digested off with T4 polymerase and subsequently cleaved with SalI. Into the so-modified vector was inserted the approximately 280 bp long N-terminal PvuII/SalI fragment of the cholesterol esterase from pCHE1. The vector M13mglEcoKCE resulted. Fusion of the mature cholesterol esterase to the signal peptide of the GBP took place via deletion mutagenesis on the single-stranded DNA of M13mglEcoKCE. By hybridisation with an oligonucleotide (SEQ.ID.NO.:4 or SEQ.ID.NO.:5), there results a partial heteroduplex DNA which is made up in vitro to the double strand and transfected into *E. coli* HB2154 (Carter et al., Nucl. Acids. Res., 13 (1985), 4431–4443). Such DNA molecules, which also contain additional sequences (GBP, EcoK cassette and 5'-untranslated cholesterol esterase sequence) between the signal peptide sequence and the mature cholesterol esterase sequence, were eliminated via EcoK selection in *E. coli* HB2154 (DSM 6541). The M13mglCE clones obtained were characterized via restriction analysis and DNA sequencing. By means of the oligonucleotides used, two different M13mglCE derivatives resulted. These were cleaved with EcoRI and XhoI and the insertion (consisting of mgl promoter, signal peptide and N-terminal region of the cholesterol esterase) cloned back into the vector pCHE1 cleaved with the appropriate enzymes. A plasmid is obtained which contains the complete sequence of the mature cholesterol esterase fused to the GBP signal peptide sequence when the oligonucleotide SEQ.ID.NO.:4 was used for the deletion mutagenesis. In the case of the use of the oligonucleotide SEQ.ID.NO.:5 for the deletion mutagenesis, the plasmid pBTmglCE (DSM 5903), which contains the amino acid Trp in position +1 of the mature cholesterol esterase sequence is obtained.

EXAMPLE 2

Changing of the Substrate Specificity by Modification of the DNA Sequence Coding for the Active Site The active centre of cholesterol esterase/lipase is defined by the amino acid sequence -Gly-His-Ser-X-Gly. This sequence, including the signal peptide, is given in the case of the *Pseudomonas spec.*-lipase/-cholesterol esterase by amino acids 109 to 113 with the sequence Gly, His, Ser, His, Gly. The active centre of a selection of lipases and cholesterol esterases is shown in Table 1.

The specificity of the cholesterol esterase can be changed by objective exchange of the amino acid X in the sequence Gly-His-Ser-X-Gly.

The sequence of the CE-coding DNA, which codes for amino acids 109–115 (including the signal sequence), reads:

Gly-His-Ser-His-Gly-Gly-Pro 5'-GGC GAC AGC CAT GGC GGC CCG-3'

The corresponding counter-strand reads:

5'-CGG GCC GCC ATG GCT GTC GCC-3'

The following nineteen oligonucleotides are used for directed mutagenesis:

| | | |
|---|---|---|
| Met 5'-CGG GCC GCC CAT GCT GTC GCC-3' | | 1. |
| Phe 5'-CGG GCC GCC GAA GCT GTC GCC-3' | | 2. |
| Gln 5'-CGG GCC GCC CTG GCT GTC GCC-3' | | 3. |
| Glu 5'-CGG GCC GCC CTC GCT GTC GCC-3' | | 4. |
| Asp 5'-CGG GCC GCC GTC GCT GTC GCC-3' | | 5. |
| Cys 5'-CGG GCC GCC GCA GCT GTC GCC-3' | | 6. |
| Ala 5'-CGG GCC GCC GGC GCT GTC GCC-3' | | 7. |
| Gly 5'-CGG GCC GCC TCC GCT GTC GCC-3' | | 8. |
| Ile 5'-CGG GCC GCC GAT GCT GTC GCC-3' | | 9. |
| Lys 5'-CGG GCC GCC CTT GCT GTC GCC-3' | | 10. |
| Leu 5'-CGG GCC GCC CAG GCT GTC GCC-3' | | 11. |
| Asn 5'-CGG GCC GCC GTT GCT GTC GCC-3' | | 12. |
| Pro 5'-CGG GCC GCC GGG GCT GTC GCC-3' | | 13. |
| Arg 5'-CGG GCC GCC GCG GCT GTC GCC-3' | | 14. |
| Ser 5'-CGG GCC GCC GGA GCT GTC GCC-3' | | 15. |
| Thr 5'-CGG GCC GCC GGT GCT GTC GCC-3' | | 16. |
| Val 5'-CGG GCC GCC GAC GCT GTC GCC-3' | | 17. |
| Trp 5'-CGG GCC GCC CCA GCT GTC GCC-3' | | 18. |
| Tyr 5'-CGG GCC GCC ATA GCT GTC GCC-3' | | 19. |

The mutagenesis is carried out according to known techniques on the M13 template (Amersham No.1523 "Oligonucleotide-directed in vitro mutagenesis system").

For this purpose, an approximately 970 bp-long SalI fragment of the CE-coding DNA from pBTmglCE is ligated into the double-stranded form of the phage DNA M13mpl9 which has been cleaved with SalI. After preparation of single-strand DNA, the corresponding oligonucleotide is hybridized on the single-strand DNA and elongation carried out in the 5'→3' direction beyond the oligonucleotide with the use of Klenow polymerase, ligase and the four nucleotide triphosphates GTP, CTP, TTP and ATP. The now double-stranded DNA is transformed in *E. coli* (from Amersham kit No. 1523 or from the mutagenesis kit of Boehringer Mannheim GmbH, cat. No. 1269046). Individual plaques are picked and the M13 phages contained therein are used for the preparation of single-strand DNA. DNA sequencing is carried out according to known techniques and thus the exact exchange to the desired mutation tested for. After preparation of double-strand DNA, the approximately 970 bp-long mutated SalI fragment is isolated. This fragment is then cloned back into the vector fragment of the plasmid pBTmglCE cleaved with SalI.

TABLE 1

| lipases/esterases from | sequence of the active centre |
|---|---|
| hog pancreas | Gly—His—Ser—Leu—Gly |
| rat tongue | Gly—His—Ser—Gln—Gly |
| Staphylococcus | Gly—His—Ser—Met—Gly |
| *Pseudomonas fragi* | Gly—His—Ser—Gln—Gly |
| *Pseudomonas spec.* | Gly—His—Ser—His—Gly |
| gastric lipase | Gly—His—Ser—Gln—Gly |

EXAMPLE 3

Expression of Lipase/Cholesterol Esterase from Pseudomonas

Plasmid pBTmglCE is cleaved with NaeI. The SacI linker d(CGTCGACG) is ligated into this cleavage position. After preparation of DNA, the successful ligation of the SacI linker is tested for by cleavage with SacI and an approximately 1800 bp-long fragment is isolated after cleavage with EcoRI and SacI. Vector pBT306.1 (preparation according to EP-A-0 187 138) is cleaved with EcoRI and SacI. The approximately 1800 bp-long fragment is ligated into this vector. The so-resulting plasmid bears the designation pBT306CE$_{His}$(wt).

This plasmid is transferred by in vivo transfer (Gene, 16 (1981), 237–247) into the Pseudomonas mutant, DSM 5902. This strain is characterised by the fact that it does not code any active cholesterol esterase. Table 2 shows the expression in various Pseudomonas strains. The determination of activity took place as described in Example 5.

EXAMPLE 4

Culturing of Micro-Organisms which Contain Cloned Cholesterol Esterase on a Plasmid The culturing of the strains takes place without inductor at 30° C. overnight in a medium which contains 16 g bactotrypton (Difco), 10 g yeast extract (Difco) and 5 g sodium chloride per liter.

Table 2 shows the cholesterol esterase activity obtained.

TABLE 2

| Pseudomonas strain | with plasmid pBT306.1 (control) | with plasmid pBT306CH$_{His}$(wt) |
|---|---|---|
| wild type P | 25* | 130 |
| DSM 5902 | 0 | 120 |
| Pseudomonas alcaligenes | 0 | 118 |

*Units/liter/OD of the culture at 550 nm with cholesterol linoleate as substrate (average of 5 independent measurements, determination to Example 6).

EXAMPLE 5

Change of the substrate specificity, activity determination

Various derivatives of cholesterol esterase were prepared as described in Example 2 by exchange of the amino acid X in the active centre. Exchange of the amino acid 112 His for glutamine leads to an increase of the activity towards the substrate cholesteryl-3-glutaric acid resorufin ester (esterase colour substrate, Example 5b).

TABLE 3

| substrate | enzyme activity with CE in which amino acid 112 is: | |
|---|---|---|
| | His | Gln |
| lipase color substrate (Example 5a) | 13.7 | 13.0 |
| esterase colour substrate (Example 5b) | 4.5 | 6.2 |
| substrate in Example 5c: | | |
| cholesteryl linoleate | 120 | 93 |
| cholesteryl octanoate | 103 | 59 |
| cholesteryl n-butyrate | 8.3 | 4.1 |
| cholesteryl oleate | 210 | 113.3 |

As can be seen from Table 3, these esterases show very different enzyme activities with respect to different substrates. This can be advantageous in the case of the reaction of substrate mixtures.

a) Lipase determination (process 1)

For the determination of lipase, 1,2-0-dilauryl-rac-glycero-3-glutaric acid resorufin ester is cleaved with lipase. The resulting glutaric acid resorufin ester hydrolyses to glutaric acid and resorufin. The extinction of resorufin is measured at 572 nm.

Reagents:

1. Substrate solution 1 mg 1,2-0-dilauryl-rac-glycero-3-glutaric acid resorufin ester dissolved in 1 ml dioxane/Thesit ® (Boehringer Mannheim, No. 836630) (1:1).

2. Buffer solution 0.1 mol/l potassium phosphate buffer, pH 6.8.

3. Sample solution 6-8 U lipase/l in potassium phosphate buffer, pH 6.8.

For the carrying out of the determination, 0.85 ml of buffer solution and 0.1 ml of substrate solution are mixed, warmed to 25° C. and the reaction started with 0.05 ml of sample solution. The extinction change at 572 nm is monitored and $\Delta E$/min. calculated from the linear range.

The lipase activity is calculated according to the following equation:

$$U/l = \frac{V \cdot 1000}{v \cdot \epsilon \cdot d} \Delta E/min$$

$V$ = test volume (1 ml)

$v$ = sample volume 0.05 ml $\epsilon$ = extinction coefficient of resorufin at 572 nm and at pH 6.8 (60.0[1 · mmol$^{-1}$ · cm$^{-1}$]

$d$ = layer thickness of the cuvette (1 cm)

$\Delta E$/min: extinction change/min.

b) Cholesterol esterase determination (process 2).

In the case of this process, the substrate cholesteryl-3-glutaric acid resorufin ester is converted with cholesterol esterase into cholesterol and glutaric acid resorufin ester. Glutaric acid resorufin ester hydrolyzes to resorufin, the color of which is measured at 572 nm.

Reagents:

1. Substrate solution 2 mg of substrate cholesteryl-3-glutaric acid resorufin ester dissolved in 1 ml dioxane/Thesit ® (1:1) and 30 μl acetic acid (2 mol/l).

2. Buffer solution 0.1 mol/l potassium phosphate buffer, pH 6.8.

3. Sample solution 3-5 U cholesterol esterase/l diluted with potassium phosphate buffer, pH 6.8.

For carrying out the determination, 0.85 ml of buffer solution and 0.05 ml of substrate solution are mixed, warmed to 25° C. and the reaction started with 0.1 ml of sample solution. The extinction change at 572 nm is monitored and $\Delta E$/min calculated from the linear range.

The cholesterol esterase activity is determined according to the equation:

$$U/l = \frac{V \cdot 1000}{v \cdot \epsilon \cdot d} \Delta E/min$$

V = test volume (1 ml)

V = sample volume (0.1 ml)

$\epsilon$ = extinction coefficient of resorufin at 572 nm and at pH 6.8 (60.0 [1·mmole$^{-1}$ ·cm$^{-1}$])

d = layer thickness of the cuvette (1 cm)

$\Delta E$/min = extinction change/min.

c) Determination of cholesterol (process 3)

According to this process, the substrate is cleaved by cholesterol esterase into cholesterol and fatty acid, the resultant cholesterol is converted with cholesterol oxidase into cholestenone and hydrogen peroxide and the resultant hydrogen peroxide is reacted with 4-aminoantipyrine and phenol to give a coloured material, the colour of which is measured at 500 nm on a photometer.

Reagents:

1. Reaction mixture 0.25 mol/l potassium phosphate buffer, pH 7.0

5 mg/ml sodium cholate 2.4 mg/ml phenol 0.4 mg/ml 4-aminoantipyrine

2. Peroxidase solution

6000 U/ml peroxidase (activity about 100 U/mg) in 0.25 mol/l potassium phosphate buffer, pH 7.0.
3. Cholesterol oxidase
25 U/ml cholesterol oxidase (activity 25 U/mg) in 1 mol/l NaCl.
4. Substrate solution
2 μmol/l of one of the following substrates:
cholesteryl linoleate
cholesteryl octanoate
cholesteryl n-butyrate
cholesteryl oleate.

For carrying out the determination, 2.5 ml of reaction mixture, 0.01 ml peroxidase solution, 0.2 ml cholesterol oxidase solution and 0.5 ml substrate solution are mixed, warmed to 37° C. and the reaction started with 0.05 ml of sample. The extinction change is monitored, ΔE/min. calculated from the linear range.

The cholesterol esterase activity is calculated as follows:

$$U/l = \frac{3.08}{\epsilon \cdot 0.05 \cdot 1} \cdot \Delta E/min \; [U/l \text{ sample solution}]$$

$\epsilon =$ extinction coefficient of the coloured material
at 500 nm: 6.89 [mmol$^{-1}$ · l · cm$^{-1}$]
ΔE/min: extinction change/min.

---

We claim:

1. Process for preparation of a cholesterol esterase, comprising mutagenizing a gene which codes for a first cholesterol esterase with an active site having amino acid sequence:

Gly-His-Ser-X-Gly to change X to an amino acid which differs from the amino acid in said first cholesterol esterase, to form a gene which codes for a second cholesterol esterase, wherein said second cholesterol esterase has substrate specificity different from said first cholesterol esterase, transforming a microorganism with said gene, and culturing said microorganism to produce said cholesterol esterase with different substrate specificity, said mutagenizing said gene being such that X is changed to His.

2. Process of claim 1, wherein said mutagenizing comprises removing an oligonucleotide sequence from said gene and replacing it by a second oligonucleotide sequence.

3. Process of claim 2, wherein said second oligonucleotide sequence is synthesized via chemical means.

4. Process of claim 2, wherein said second oligonucleotide sequence is synthesized via solid phase synthesis.

5. Process of claim 2, wherein said second oligonucleotide sequence is synthesized via a phosphoramidite process.

6. Process of claim 2, comprising ligating said second oligonucleotide sequence into said gene.

7. Process of claim 1, wherein said microorganism does not express active cholesterol esterase prior to transformation.

8. Process of claim 1, wherein said microorganism produces cholesterol esterase, and said process further comprises mutagenizing said microorganism so it does not produce cholesterol esterase prior to transforming said microorganism with said gene.

9. Process of claim 8, wherein said microorganism is *E. coli* or *Pseudomonas spec.*

10. Process of claim 9, wherein said microorganism is *Pseudomonas spec* DSM 5902.

11. Process of claim 1, comprising introducing said mutagenized gene into said microorganism via a vector.

12. Process of claim 11, wherein said vector is pBR322 or pBT306.1.

13. Non naturally occurring cholesterol esterase produced according to the process of claim 1.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 1721 base pairs
        ( B ) TYPE: nucleic acid
        ( C ) STRANDEDNESS: double
        ( D ) TOPOLOGY: linear ( v i ) ORIGINAL SOURCE:
        ( A ) ORGANISM: Pseudomonas spec.

( x i ) SEQUENCE DESCRIPTION: SEQ ID NO:1:

```
ACGCCAACCA GCGCTTAGCG AATTCAGCGC TGCAAACAAC ACCCTGTGCG CCCCGCAAGT        60

AGCTGTTTAA ATCGGCGCAG GGCGCATCCT AGAGACTCCC ACGCAGGACT GTCAAGGCGC       120

GCCATCATCG CACCCCAACC TTCGATTGGC CGCCTCACAT TTCCACCGCT GGACGCGGGT       180

CAAACGCTCC GCCTGCACTC GTCAAACCGC TGCCGAGCTG AACGATTGCG GCCTGCCATC       240

ACAGCTCGGC TGTGTCGCCA CGTAACAGAA AAGCTGCCGC AATCTCGCTG ACAAAACAGG       300

GTTATCTTCG GGAAAGCGCC GCAATAGAGG GGTTAATCGG GAAAACCTGG CGATGGCATG       360

TTTCCTGCCA TCGTTCTGTC GCCGTACGTG CCATGGGATG GGCACGCTTG TGTTGCAGGA       420

TGCAGCCTGA CTGCTAATAA ACCCATCGAG AGCGCC ATG AAG AAC AAT AAA ACC         474
                                        Met Lys Asn Asn Lys Thr
                                        -24              -20
```

```
CTG CTC GCC CTC TGC CTC GGC GCC GGC CTG CTC GCC AGC GGC CAG ACC        522
Leu Leu Ala Leu Cys Leu Gly Ala Gly Leu Leu Ala Ser Gly Gln Thr
            -15                 -10                  -5

CAG GCT TTC TGG TTC GGT TCG TCC GGC TAT ACC CAG ACC AAA TAC CCC        570
Gln Ala Phe Trp Phe Gly Ser Ser Gly Tyr Thr Gln Thr Lys Tyr Pro
        1              5                       10

ATC GTC CTC GGC CAC GGC ATG CTG GGT TTC GAC AGC ATC CTC GGC GTC        618
Ile Val Leu Gly His Gly Met Leu Gly Phe Asp Ser Ile Leu Gly Val
15                  20                  25                      30

GAC TAC TGG TAT GGC ATC CCG ACC GCT CTA CGC CGC GAC GGC GCC AGC        666
Asp Tyr Trp Tyr Gly Ile Pro Thr Ala Leu Arg Arg Asp Gly Ala Ser
                    35                  40                  45

GTC TAC GTG ACC GAA GTC AGC CAG TTG GAC ACC TCT GAA GCA CGC GGC        714
Val Tyr Val Thr Glu Val Ser Gln Leu Asp Thr Ser Glu Ala Arg Gly
            50                  55                  60

GAA CAA TTG CTG CAG CAG GTA GAG GAC ATC GTC GCC ATC AGC GGC AAG        762
Glu Gln Leu Leu Gln Gln Val Glu Asp Ile Val Ala Ile Ser Gly Lys
        65                  70                  75

GGC AAG GTC AAT CTG ATC GGC CAC AGC CAT GGC GGC CCG ACC ACC CGC        810
```

```
Gly Lys Val Asn Leu Ile Gly His Ser His Gly Gly Pro Thr Thr Arg
     80                  85                  90

TAT GTC GCC GCC GTG CGC CCG GAT CTG GTC GCT TCG GTC ACC AGC GTC    858
Tyr Val Ala Ala Val Arg Pro Asp Leu Val Ala Ser Val Thr Ser Val
 95                 100                 105                 110

GGC GCT CCG CAC AAG GGT TCG GCC ACT GCA GAC TTC CTC AAG GGC ATC    906
Gly Ala Pro His Lys Gly Ser Ala Thr Ala Asp Phe Leu Lys Gly Ile
                115                 120                 125

AGC GAC GGC CCT GCC GGG CCG GTA GCG ACC CCG GTG CTG GCA GGC ATC    954
Ser Asp Gly Pro Ala Gly Pro Val Ala Thr Pro Val Leu Ala Gly Ile
            130                 135                 140

ATC AAC GGC CTG GGC GCG CTG ATC AAC TTC CTC TCC GGC AGC CCC AGC   1002
Ile Asn Gly Leu Gly Ala Leu Ile Asn Phe Leu Ser Gly Ser Pro Ser
        145                 150                 155

ACC ACA CCG CAG AAC GCG CTC GGC TCG CTG GAG TCG CTC AAC AGT CAA   1050
Thr Thr Pro Gln Asn Ala Leu Gly Ser Leu Glu Ser Leu Asn Ser Gln
160                 165                 170

GGT GCC GCT CGC TTC AAC GCC AAG TTC CCG CAG GGC ATC CCG ACC AGC   1098
Gly Ala Ala Arg Phe Asn Ala Lys Phe Pro Gln Gly Ile Pro Thr Ser
175                 180                 185                 190

GCC TGC GGC GAA GGC GCC TAC AGC GTG AAC GGC GTG CGT TAC TAC TCG   1146
Ala Cys Gly Glu Gly Ala Tyr Ser Val Asn Gly Val Arg Tyr Tyr Ser
                195                 200                 205

TGG AGC GGC ACC AGC CCG TTG ACC AAC CTG CTC GAC CCG AGC GAC CTG   1194
Trp Ser Gly Thr Ser Pro Leu Thr Asn Leu Leu Asp Pro Ser Asp Leu
            210                 215                 220

CTG ATG GGC GCG TCC TCG TTG ACC TTC GGC AGC GAA GCC AAC GAG CCT   1242
Leu Met Gly Ala Ser Ser Leu Thr Phe Gly Ser Glu Ala Asn Glu Pro
        225                 230                 235

GGT CGG CCG CTG CAG TTC GCG CAT GGG CCA GTC ATT CGT GAC AAC TAC   1290
Gly Arg Pro Leu Gln Phe Ala His Gly Pro Val Ile Arg Asp Asn Tyr
    240                 245                 250

CGG ATG AAC CAC CTC GAC GAG GTC AAC CAG ACG CTG GGG CTG ACC AGC   1338
Arg Met Asn His Leu Asp Glu Val Asn Gln Thr Leu Gly Leu Thr Ser
255                 260                 265                 270

CTG TTC GAG ACC GAC CCG GTG ACC GTC TAC CGT CAA CAC GCC AAC CGC   1386
Leu Phe Glu Thr Asp Pro Val Thr Val Tyr Arg Gln His Ala Asn Arg
                275                 280                 285

CTG AAA AAC GCC GGG CTC TAGGCTAACG GATAACTTCC GCCCGAGCCG          1434
Leu Lys Asn Ala Gly Leu
                290

TGCGCATCGA GACATCGGTG CACGGCGCAT CCTACCCCTG ACATCCAGAG CCACACGTGA 1494

AGAAAGCCCT ATTCGCCCTG CCTCTACTGA TCGGCGCCGG CCTGGCGTTG ATGCTTTACC 1554

TGCAACCCGG ACATCAGCCC ACCCACGTCA GCTCTCCTGC CACGGCTACA GTGACGAAAC 1614

CTGTGCCGCA GGCACCTGCC GAAGCCATGA CGCCGGCTGC AAGTGACACG CAGAAGAAGG 1674

CGCCCAAACT GGCCCTGCCC GCCTCCTTCG CCGGCACCGA CGTCGAC             1721
```

( 2 ) INFORMATION FOR SEQ ID NO:2:

( i ) SEQUENCE CHARACTERISTICS:
        ( A ) LENGTH: 316 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Lys Asn Asn Lys Thr Leu Leu Ala Leu Cys Leu Gly Ala Gly Leu
-24                 -20                 -15                 -10

Leu Ala Ser Gly Gln Thr Gln Ala Phe Trp Phe Gly Ser Ser Gly Tyr
         -5                   1                   5
```

| | | | | | | | | | | | | | | |
|---|---|---|---|---|---|---|---|---|---|---|---|---|---|---|
| Thr | Gln | Thr | Lys | Tyr | Pro | Ile | Val | Leu | Gly | His | Gly | Met | Leu | Gly | Phe |
| | 10 | | | | 15 | | | | | | 20 | | | | |
| Asp | Ser | Ile | Leu | Gly | Val | Asp | Tyr | Trp | Tyr | Gly | Ile | Pro | Thr | Ala | Leu |
| 25 | | | | | 30 | | | | 35 | | | | | | 40 |
| Arg | Arg | Asp | Gly | Ala | Ser | Val | Tyr | Val | Thr | Glu | Val | Ser | Gln | Leu | Asp |
| | | | | 45 | | | | | 50 | | | | | 55 | |
| Thr | Ser | Glu | Ala | Arg | Gly | Glu | Gln | Leu | Leu | Gln | Gln | Val | Glu | Asp | Ile |
| | | | 60 | | | | | 65 | | | | | 70 | | |
| Val | Ala | Ile | Ser | Gly | Lys | Gly | Lys | Val | Asn | Leu | Ile | Gly | His | Ser | His |
| | | 75 | | | | | 80 | | | | | | 85 | | |
| Gly | Gly | Pro | Thr | Thr | Arg | Tyr | Val | Ala | Ala | Val | Arg | Pro | Asp | Leu | Val |
| | 90 | | | | | 95 | | | | | 100 | | | | |
| Ala | Ser | Val | Thr | Ser | Val | Gly | Ala | Pro | His | Lys | Gly | Ser | Ala | Thr | Ala |
| 105 | | | | | 110 | | | | | 115 | | | | | 120 |
| Asp | Phe | Leu | Lys | Gly | Ile | Ser | Asp | Gly | Pro | Ala | Gly | Pro | Val | Ala | Thr |
| | | | | 125 | | | | | 130 | | | | | 135 | |
| Pro | Val | Leu | Ala | Gly | Ile | Ile | Asn | Gly | Leu | Gly | Ala | Leu | Ile | Asn | Phe |
| | | | 140 | | | | | 145 | | | | | 150 | | |
| Leu | Ser | Gly | Ser | Pro | Ser | Thr | Thr | Pro | Gln | Asn | Ala | Leu | Gly | Ser | Leu |
| | | 155 | | | | | 160 | | | | | 165 | | | |
| Glu | Ser | Leu | Asn | Ser | Gln | Gly | Ala | Ala | Arg | Phe | Asn | Ala | Lys | Phe | Pro |
| | 170 | | | | | 175 | | | | | | 180 | | | |
| Gln | Gly | Ile | Pro | Thr | Ser | Ala | Cys | Gly | Glu | Gly | Ala | Tyr | Ser | Val | Asn |
| 185 | | | | | 190 | | | | | 195 | | | | | 200 |
| Gly | Val | Arg | Tyr | Tyr | Ser | Trp | Ser | Gly | Thr | Ser | Pro | Leu | Thr | Asn | Leu |
| | | | | 205 | | | | | 210 | | | | | 215 | |
| Leu | Asp | Pro | Ser | Asp | Leu | Leu | Met | Gly | Ala | Ser | Ser | Leu | Thr | Phe | Gly |
| | | | 220 | | | | | 225 | | | | | 230 | | |
| Ser | Glu | Ala | Asn | Glu | Pro | Gly | Arg | Pro | Leu | Gln | Phe | Ala | His | Gly | Pro |
| | | 235 | | | | | 240 | | | | | 245 | | | |
| Val | Ile | Arg | Asp | Asn | Tyr | Arg | Met | Asn | His | Leu | Asp | Glu | Val | Asn | Gln |
| | 250 | | | | | 255 | | | | | 260 | | | | |
| Thr | Leu | Gly | Leu | Thr | Ser | Leu | Phe | Glu | Thr | Asp | Pro | Val | Thr | Val | Tyr |
| 265 | | | | | 270 | | | | | 275 | | | | | 280 |
| Arg | Gln | His | Ala | Asn | Arg | Leu | Lys | Asn | Ala | Gly | Leu | | | | |
| | | | | 285 | | | | | 290 | | | | | | |

( 2 ) INFORMATION FOR SEQ ID NO:3:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
AATTCTATGT TCTGGTTCGG CTCGAGCGGC TATACCCAGA CCAAATACCC CATCGTCCTA      60

GGCCACGGCA TGCTGGGTTT CGACAGCATC CTCGGCG                              97
```

( 2 ) INFORMATION FOR SEQ ID NO:4:

( i ) SEQUENCE CHARACTERISTICS:
        ( A ) LENGTH: 97 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
TCGACGCCGA GGATGCTGTC GAAACCCAGC ATGCCGTGGC CTAGGACGAT GGGGTATTTG      60
```

```
GTCTGGGTAT AGCCGCTCGA GCCGAACCAG AACATAG                                                97
```

( 2 ) INFORMATION FOR SEQ ID NO:5:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( x i ) SEQUENCE DESCRIPTION: SEQ ID NO:5:

```
GAGCCGAACC AGAAAGCCGC GTGCGC                                                            26
```

( 2 ) INFORMATION FOR SEQ ID NO:6:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( x i ) SEQUENCE DESCRIPTION: SEQ ID NO:6:

```
CTCGAGCCGA ACCAAGCCGC GTGCGC                                                            26
```